(12) United States Patent
Sanroma et al.

(10) Patent No.: US 10,324,030 B2
(45) Date of Patent: Jun. 18, 2019

(54) PORTABLE MOISTURE ANALYZER FOR NATURAL GAS

(71) Applicant: GE Infrastructure Sensing, LLC, Billerica, MA (US)

(72) Inventors: John Sanroma, Billerica, MA (US); John Poole, Billerica, MA (US); Aniruddha Sudheer Weling, Billerica, MA (US); Gene Berkowitz, Billerica, MA (US)

(73) Assignee: GE Infrastructure Sensing, LLC, Billerica, MA (US)

( * ) Notice: Subject to any disclaimer, the term of this patent is extended or adjusted under 35 U.S.C. 154(b) by 0 days.

(21) Appl. No.: 15/854,495

(22) Filed: Dec. 26, 2017

(65) Prior Publication Data

US 2018/0238797 A1    Aug. 23, 2018

Related U.S. Application Data

(60) Provisional application No. 62/439,273, filed on Dec. 27, 2016.

(51) Int. Cl.
*G01N 21/39* (2006.01)
*G01N 1/34* (2006.01)
(Continued)

(52) U.S. Cl.
CPC .............. *G01N 21/39* (2013.01); *G01N 1/34* (2013.01); *G01N 21/01* (2013.01);
(Continued)

(58) Field of Classification Search
CPC .... G01N 21/39; G01N 21/01; G01N 33/0016; G01N 33/22; G01N 1/2247; G01N 2201/0221; G01N 33/246; G01J 3/42
See application file for complete search history.

(56) References Cited

U.S. PATENT DOCUMENTS

D221,001 S   6/1971  Sylvester
D238,562 S   1/1976  Sylvester
(Continued)

OTHER PUBLICATIONS

International Search Report and Written Opinion issued in corresponding International Application No. PCT/US2017/068428, dated Mar. 8, 2018, 12 pages.
(Continued)

*Primary Examiner* — Maurice C Smith
(74) *Attorney, Agent, or Firm* — Mintz Levin Cohn Ferris Glovsky and Popeo, P.C.

(57) ABSTRACT

Methods, devices, and systems are provided for analyzing the moisture content in natural gas. In one embodiment, a portable moisture analyzer system is provided and can include a moisture analyzer and a housing. The moisture analyzer can include a tunable diode laser absorption spectrometer (TDLAS) and a natural gas sample conditioning system. The TDLAS can be configured to detect water vapor content within a natural gas sample. The sample conditioning system can be in fluid communication with the TDLAS and can be configured to condition at least one of temperature, flow rate, and pressure of a natural gas sample. The housing can be configured to receive the moisture analyzer therein and to protect the moisture analyzer from vibration and/or shock.

21 Claims, 7 Drawing Sheets

(51) Int. Cl.
*G01N 21/01* (2006.01)
*G01N 33/00* (2006.01)
*G01N 33/22* (2006.01)
*G01N 1/22* (2006.01)
*G01N 21/15* (2006.01)
*G01N 21/3504* (2014.01)
*G01N 21/85* (2006.01)

(52) U.S. Cl.
CPC ....... *G01N 33/0016* (2013.01); *G01N 33/225* (2013.01); *G01N 1/2247* (2013.01); *G01N 21/15* (2013.01); *G01N 2021/354* (2013.01); *G01N 2021/399* (2013.01); *G01N 2021/8578* (2013.01); *G01N 2201/0221* (2013.01); *G01N 2201/06113* (2013.01); *G01N 2201/1211* (2013.01); *G01N 2201/1214* (2013.01); *G01N 2201/1218* (2013.01)

(56) References Cited

U.S. PATENT DOCUMENTS

| | | | |
|---|---|---|---|
| 4,589,971 A | 5/1986 | Mayeaux | |
| 4,765,193 A | 8/1988 | Holden et al. | |
| 4,786,472 A | 11/1988 | McConnell et al. | |
| D318,627 S | 7/1991 | Frederick | |
| D319,987 S | 9/1991 | Ueno | |
| 5,305,231 A | 4/1994 | Coppler et al. | |
| 5,525,799 A * | 6/1996 | Andresen | H01J 49/0022 250/281 |
| 6,042,634 A | 3/2000 | Van Tassel et al. | |
| 6,047,602 A | 4/2000 | Lynnworth | |
| D518,393 S | 4/2006 | Nesenoff | |
| 7,422,909 B2 * | 9/2008 | Schur | G01N 1/2273 436/177 |
| 7,581,453 B2 | 9/2009 | Ao et al. | |
| 7,750,502 B1 | 7/2010 | Haun et al. | |
| 7,942,068 B2 | 5/2011 | Ao et al. | |
| 7,954,387 B1 | 6/2011 | Furlong | |
| 8,054,094 B1 | 11/2011 | Langoju et al. | |
| 8,121,804 B2 | 2/2012 | Mahalingam et al. | |
| 8,264,246 B2 | 9/2012 | Mahalingam et al. | |
| 8,429,985 B2 | 4/2013 | Furlong | |
| 8,508,238 B2 | 8/2013 | Mahalingam et al. | |
| 8,511,144 B2 | 8/2013 | Goravar et al. | |
| 8,547,554 B2 | 10/2013 | Liu et al. | |
| 8,726,739 B2 | 5/2014 | May et al. | |
| D708,530 S * | 7/2014 | Noda | D10/81 |
| 8,855,947 B2 | 10/2014 | Sheila-Vadde et al. | |
| 8,892,379 B2 | 11/2014 | Langoju et al. | |
| 8,919,209 B2 | 12/2014 | Furlong | |
| 8,963,562 B2 | 2/2015 | Basu et al. | |
| 8,978,476 B2 | 3/2015 | Ao et al. | |
| 9,051,727 B1 | 6/2015 | Carlton et al. | |
| 9,234,777 B2 | 1/2016 | Ao et al. | |
| 9,297,679 B2 | 3/2016 | Furlong et al. | |
| D753,522 S | 4/2016 | Griffiths et al. | |
| 9,343,055 B2 | 5/2016 | Ao et al. | |
| 9,347,807 B2 | 5/2016 | Ao et al. | |
| 9,435,782 B2 | 9/2016 | Lenz et al. | |
| 2002/0152797 A1 * | 10/2002 | McAndrew | F17D 1/04 73/23.2 |
| 2004/0079887 A1 | 4/2004 | May | |
| 2007/0246653 A1 | 10/2007 | Zhou | |
| 2007/0273882 A1 * | 11/2007 | Smith | G01N 21/39 356/437 |
| 2008/0123712 A1 * | 5/2008 | Zhou | G01N 21/39 372/55 |
| 2008/0281528 A1 | 11/2008 | Relle, Jr. | |
| 2010/0171505 A1 | 7/2010 | Norgaard et al. | |
| 2013/0029333 A1 * | 1/2013 | Son | C12Q 1/6813 435/6.11 |
| 2014/0260659 A1 | 9/2014 | Sheila-Vadde et al. | |
| 2015/0097579 A1 | 4/2015 | Sharma et al. | |
| 2015/0316452 A1 | 11/2015 | Progar | |
| 2016/0131601 A1 | 5/2016 | Sharma et al. | |

OTHER PUBLICATIONS

GE Oil & Gas. Safire 2.0 Multiphase Flow Meter Brochure (2015).
GE Oil & Gas. Safire 2.0 Multiphase Flow Meter Datasheet (2015).
U.S. Appl. No. 62/310,333, filed Mar. 18, 2016, Sanroma et al.
U.S. Appl. No. 62/334,531, filed May 11, 2016, Ao et al.

* cited by examiner

PORTABLE MOISTURE ANALYZER FOR NATURAL GAS

CROSS-REFERENCE TO RELATED APPLICATIONS

This application claims the benefit of U.S. Provisional Patent Application No. 62/439,273, filed on Dec. 27, 2016, entitled "Portable Moisture Analyzer For Natural Gas," which is incorporated by reference in its entirety.

BACKGROUND

Moisture, such as water vapor, can be an undesirable component found in natural gas extracted from underground. In one aspect, water vapor can reduce the fuel value (energy generated by combustion per unit mass) of the natural gas. In another aspect, the water vapor can condense into liquid and this liquid can cause corrosion of natural gas extraction, transport, and storage equipment. In a further aspect, liquid water can damage equipment utilizing the natural gas, such as turbines. For these reasons, it can be desirable to limit the concentration of water vapor present in a natural gas stream.

In some instances, it can be standard practice to periodically or continuously measure water vapor concentration of a natural gas stream at different locations of a gas extraction system, such as extraction sites, pipelines, and storage sites, to verify that the natural gas stream at these locations meets water vapor content limits. In one example, fixed monitoring facilities can be established for natural gas measurement on-site. In another example, natural gas samples can be acquired and transported to a remote laboratory for analysis.

SUMMARY

In general, devices, systems, and methods and devices are provided for determining the moisture content of gas extracted from a gas source and, in particular, natural gas flowing through a pipeline.

In one embodiment, a portable moisture analyzer system is provided and it can include a moisture analyzer, an inner housing, and an outer housing. The moisture analyzer can include a moisture sensor, a fluid conduit network, a sample conditioning system, and an instrument panel. The moisture sensor can be configured to detect water vapor content within a gas sample and output a moisture signal including data representing the detected water vapor content. The fluid conduit network can be in fluid communication with the moisture sensor and the fluid conduit network can extend between an inlet and an outlet. The fluid conduit network can also be configured to receive, at the inlet, a flow of a raw gas sample from a gas source. The sample conditioning system can include one or more conditioning devices positioned along the fluid conduit network, between the inlet and the moisture sensor. The conditioning devices can be configured to adjust at least one of pressure and flow rate of a raw gas sample flow received by the fluid conduit network and filter particulate and liquid contaminants from the raw gas sample flow to provide a conditioned gas sample flow to the moisture sensor. The instrument panel can include opposed first and second sides. Each of the conditioning devices and a portion of the fluid conduit network can be mounted on the first side of the instrument panel. The inner housing can define one or more inner housing cavities dimensioned to receive a portion of the moisture analyzer including the moisture sensor, and the inner housing can be coupled to the first side of the instrument panel. The outer housing can define an outer housing cavity dimensioned to receive the inner housing and the moisture analyzer. The outer housing and the inner housing can be configured to attenuate vibration transmitted therethrough to the moisture sensor.

In another embodiment, the outer housing can include a base and a lid configured to reversibly seal to the base. The outer housing can be substantially fluid-tight when the lid is sealed to the base.

In another embodiment, the moisture sensor can include a laser absorption spectrometer. The spectrometer can include a reversibly attachable portion including a mirror. The inner housing can also include a channel extending through a sidewall that can be dimensioned for receipt of the reversibly attachable portion. The spectrometer can be positioned within the inner housing such that the reversibly attachable portion can be accessible through the channel.

In another embodiment, the fluid conduit network can include a plurality of conduits forming an inlet portion, a conditioning portion, a sensor portion, and an outlet portion. The inlet portion can extend between the inlet and the conditioning portion and the inlet portion can be mounted on the first side of the instrument panel. The conditioning portion can extend between the inlet portion and the sensor portion and the conditioning portion can be mounted on the first side of the instrument panel. The conditioning devices can be positioned along the conditioning portion. The sensor portion can extend between the conditioning portion and the outlet portion. The moisture sensor can be positioned along the sensor portion. The outlet portion can extend between the sensor portion and the outlet, and the outlet portion can be mounted on the first side of the instrument panel.

In another embodiment, the inlet portion can include an isolation valve configured to regulate the raw flow rate within the moisture analyzer under control of an isolation control interface. The isolation control interface can be accessible from the second side of the instrument panel.

In another embodiment, the inlet portion further can include an inlet pressure gage configured to measure pressure of the raw gas sample flow prior to receipt by the conditioning portion. The inlet pressure gage can be mounted to the instrument panel and readable from the second side of the instrument panel.

In another embodiment, the one or more conditioning devices can include a separator configured to filter liquids from the raw gas sample flow and provide a filtered gas sample flow having a liquid content less than a threshold liquid volume.

In another embodiment, the fluid conduit network can also include a bypass portion extending between the first conditioning device and the outlet. The bypass portion can include a bypass valve. The bypass portion can be configured to receive a bypass flow including liquids filtered from the raw gas sample at a bypass flow rate. The bypass valve can be configured to regulate the bypass flow rate under control of a bypass control interface accessible from the second side of the instrument panel.

In another embodiment, the separator can be accessible through the second side of the instrument panel for removal from the sample conditioning system.

In another embodiment, the separator can be configured to substantially inhibit a flow of a raw gas sample causing a pressure drop exceeding a threshold pressure decrease from entering the conditioning portion.

In another embodiment, the one or more conditioning devices can include a sample valve interposed between the separator and the moisture sensor. The sample valve can be configured to regulate a flow rate of the filtered gas sample flow under control of a sample control interface. The sample control interface can be accessible from the second side of the instrument panel. The sample valve can provide a conditioned gas sample flow having a flow rate within a predetermined flow rate range.

In another embodiment, the fluid conduit network can include a relief portion extending between the inlet portion and a relief outlet and a relief vent positioned along the relief portion. The relief vent can be configured to permit the flow of raw gas from the inlet portion to the relief outlet under control of a relief control interface. The relief control interface can be accessible from the second side of the instrument panel.

The plurality of conduits can include a first set of conduits forming the inlet portion, the conditioning portion, and outlet portion and a second set of conduits forming the sensor portion. At least a portion of the second set of conduits can be less rigid than the first set of conduits.

In another embodiment, the portable moisture analyzer system can include a temperature sensor, a pressure sensor, and a controller. The temperature sensor can be configured to output a temperature signal including data representing a measured temperature of a conditioned gas sample flow received by the moisture sensor. The pressure sensor can be configured to output a pressure signal including data representing a measured pressure of a conditioned gas sample flow received by the moisture sensor. The controller can be configured to receive the moisture signal, the temperature signal and the pressure signal, and determine an adjusted moisture content for the conditioned gas sample flow based upon the received moisture signal, temperature signal, and pressure signal.

In another embodiment, the weight of the portable moisture analyzer system can be less than or equal to 50 lbs.

Methods for moisture content analysis are also provided. In one embodiment, a method can include opening a reversibly sealable outer housing of a moisture analyzer system to reveal an instrument panel. In another embodiment, the method can include providing, from a gas source to an inlet of the moisture analyzer positioned on the instrument panel, a raw gas sample flow at a raw gas pressure and a raw gas flow rate. In a further embodiment, the method can include adjusting, by a sample conditioning system of a moisture analyzer disposed within an outer housing cavity in the outer housing, at least one of the raw gas pressure and the raw gas flow rate to provide a conditioned gas sample flow. At least a portion of a sample conditioning system can be mounted to a first side of an instrument panel of the moisture analyzer, and one or more user interface objects configured to control the sample conditioning system can be mounted to a second side of the instrument panel. In a further embodiment, the method can include receiving, by a moisture sensor of the moisture analyzer, the conditioned gas sample from the sample conditioning system. The moisture sensor can be mounted within and spaced apart from an inner housing mounted to the first side of the instrument panel. The outer housing and the inner housing can be configured to attenuate vibration transmitted therethrough to the moisture sensor.

In another embodiment, the method can include receiving, by a controller in communication with the moisture sensor, a moisture signal, a pressure signal, and a temperature signal, each signal respectively including data representing a moisture content, a pressure, and a temperature of the conditioned gas sample flow received by the moisture sensor. The method can also include determining, by the controller, an adjusted moisture content based upon the received moisture signal, temperature signal, and pressure signal.

In another embodiment, the gas source can be a natural gas pipeline.

In another embodiment, the method can also include, prior to providing the raw gas sample flow to the inlet of the moisture analyzer, transporting the moisture analyzer system to the site of the gas pipeline. The portable moisture analyzer can weigh less than or equal to fifty lbs.

In another embodiment, the moisture sensor can include a spectrometer including a reversibly attachable portion including a mirror. The inner housing can also include a channel extending through a sidewall that can be dimensioned for receipt of the reversibly attachable portion. The spectrometer can be positioned within the inner housing such that the reversibly attachable portion can be accessible through the channel when the inner housing and the moisture analyzer are removed from the outer housing while coupled together.

DESCRIPTION OF DRAWINGS

These and other features will be more readily understood from the following detailed description taken in conjunction with the accompanying drawings, in which.

It is noted that the drawings are not necessarily to scale. The drawings are intended to depict only typical aspects of the subject matter disclosed herein, and therefore should not be considered as limiting the scope of the disclosure.

DETAILED DESCRIPTION

Moisture, such as water vapor, can be an undesirable component found in natural gas extracted from underground. It can be desirable to measure the moisture content of extracted natural gas to ensure that this moisture content does not exceed certain limits. Moisture content measurements can involve removing a natural gas sample from a natural gas stream (e.g., from a pipeline), conditioning the natural gas sample, and providing the conditioned natural gas sample to an analyzer to determine its moisture content. Conditioning can adjust one or more parameters of the natural gas sample, such as flow rate, pressure, and temperature, to within predetermined ranges that are suitable for safe operation of the analyzer and ensure that moisture content measurements of different samples are made under nominally identical conditions. However, some existing measurement approaches, such as fixed, on-site facilities and transportation of natural gas samples to remote laboratory facilities are problematic. In one example, fixed facilities can be costly to establish and operate. In another example, transporting natural gas samples can be time consuming and carries a risk of sample contamination. These challenges can be further magnified when natural gas samples are to be measured at remote locations, such as pipelines. Accordingly, a portable moisture analyzer system and methods for using the same are provided. The portable moisture analyzer system can include a moisture sensor and a sample conditioning system in a self-contained form factor and housed within protective enclosures. The protective enclosures can be configured to protect the moisture sensor and a sample conditioning system from vibration and shock, facilitating transport from one test point to another on a natural gas pipeline while concurrently preserving sample conditioning functionality, safety, measurement speed, and measurement accuracy.

Embodiments of the portable moisture analyzer system are discussed below in the context of measuring water vapor content of natural gas samples received from a pipeline. However, the disclosed embodiments can be employed for measurement of gas samples received from any gas source. Further, the disclosed embodiments can be configured to measure trace level of contaminants in natural gas samples other than water vapor without limit.

Figure 1:
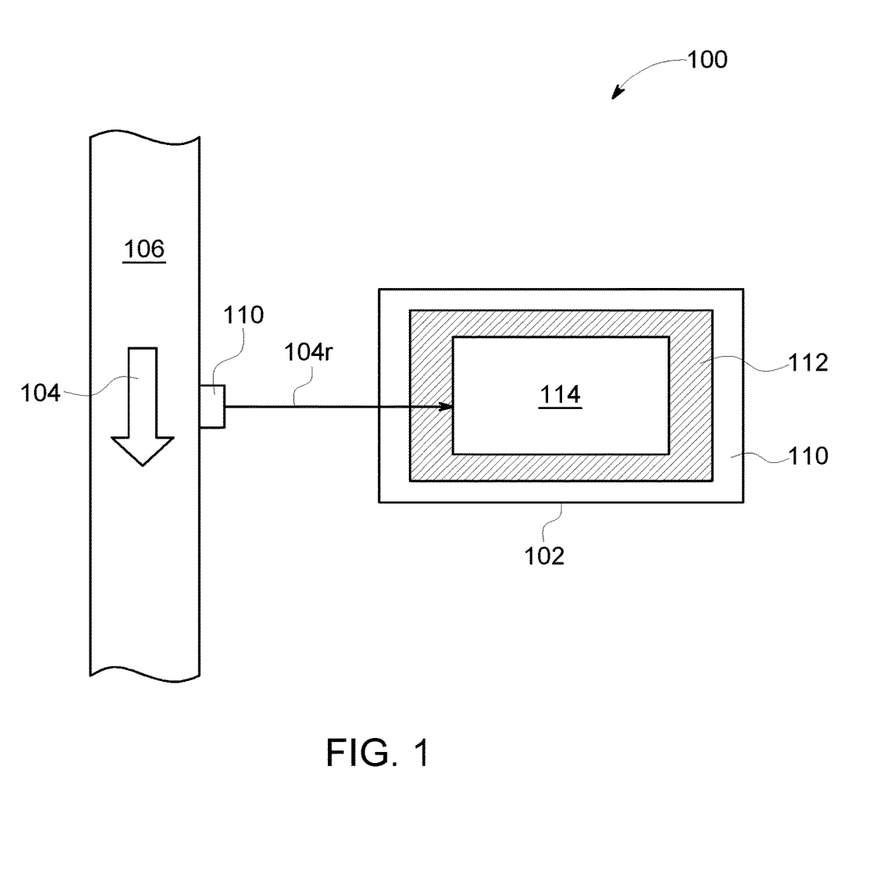
FIG. 1 is a schematic illustration of one exemplary embodiment of an operating environment including a portable moisture analyzer system.

FIG. 1 illustrates one exemplary embodiment of an operating environment 100 including a portable moisture analyzer system 102 configured to measure moisture content of a flow of natural gas 104 contained within a pipeline 106. The pipeline 106 can include a port 108 configured to allow extraction of a flow of natural gas flow from the pipeline, referred to as a raw natural gas sample flow or raw sample flow 104r. The portable moisture analyzer system 102 can include an outer housing 110, an inner housing 112, and a moisture analyzer 114. As discussed in detail below, the outer housing 110 can be reversibly sealed and configured to contain the inner housing 112 and the moisture analyzer 114, while the inner housing 112 can also be coupled to a portion of the moisture analyzer 114.

Prior to use, the portable moisture analyzer system 102 can be transported to a designated pipeline location with the outer housing 110 in a sealed position. During transport, the outer housing 110 can protect the moisture analyzer 114 from the environment. In certain embodiments, when in the sealed state, the outer housing 110 can provide ingress protection at an IP66 level, as defined by international standard EN 60529 (e.g., British BS EN 60529:1992, European IEC 60509:1989). The IP66 protection level represents intrusion protection sufficient to protect against dust that can harm electrical equipment and moisture protection sufficient to protect against low pressure water jets in all directions. The outer housing 110 and the inner housing 112 can further protect the moisture analyzer 114 from vibration and shock encountered during transport.

In use, the outer housing 110 can be opened to provide access to the moisture analyzer 114. The pipeline 106 can be placed in fluid communication with the moisture analyzer 114 (e.g., via a conduit) to provide the raw sample flow 104r. Upon receipt of a raw sample flow 104r, the moisture analyzer 114 can condition one or more of the flow rate, pressure, and temperature of the raw sample flow to provide a conditioned sample flow. This conditioned sample flow can be subsequently analyzed to determine its moisture content.

Figure 2:
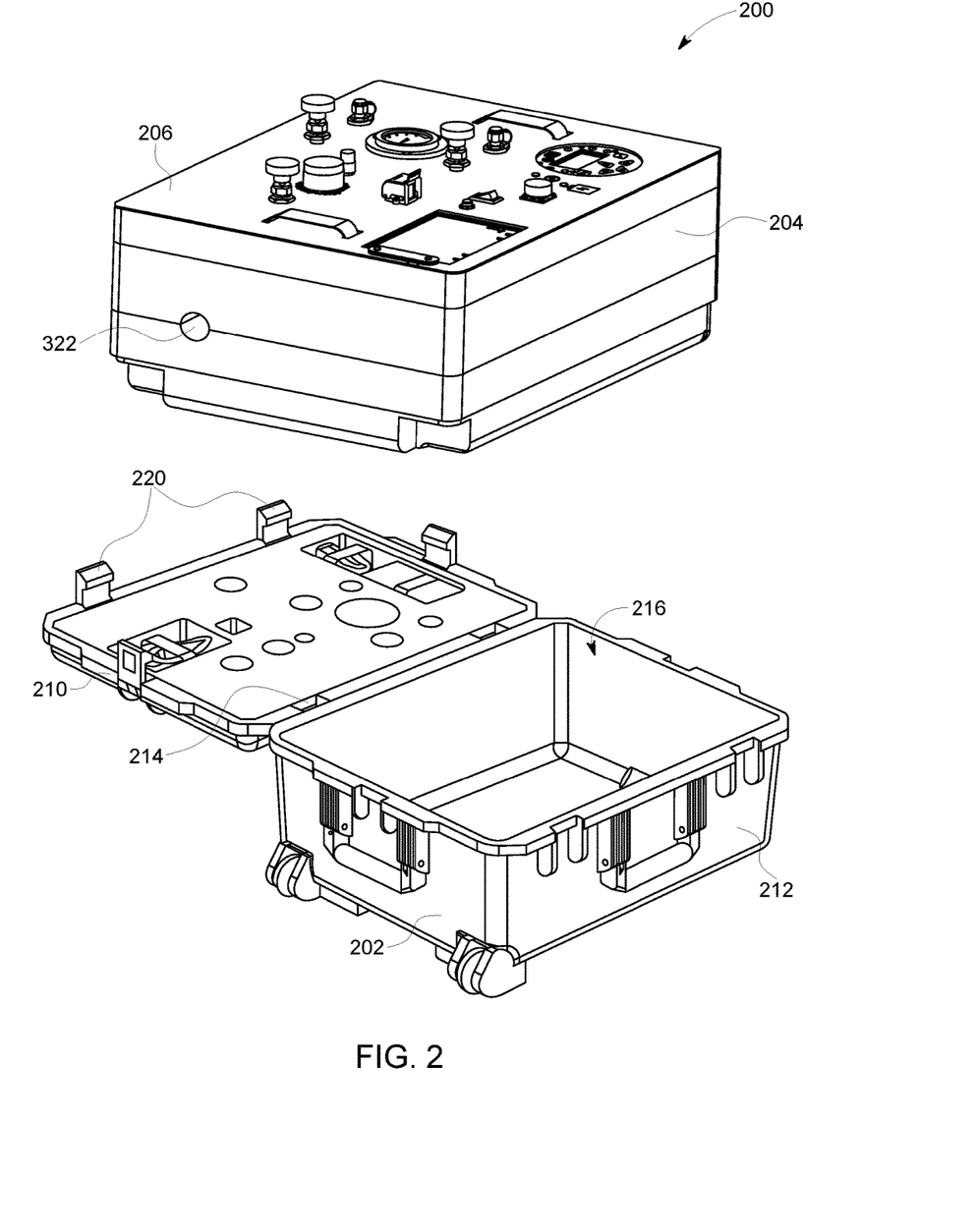
FIG. 2 is a perspective, disassembled view of one exemplary embodiment of the portable moisture analyzer system of FIG. 1 including an outer housing, an inner housing, and a moisture analyzer.

FIG. 2 is a perspective, disassembled view of one exemplary embodiment of a portable moisture analyzer system 200 illustrating an outer housing 202, an inner housing 204, and a moisture analyzer 206 in a disassembled view. As shown, the outer housing 202 is formed in a briefcase-like form factor having a lid 210 pivotably attached to a base 212 at a hinge 214. The base 212 can define an outer housing cavity 216 dimensioned to receive the inner housing 204 and the moisture analyzer 206. The lid 210 can pivot between an open position, allowing access to the moisture analyzer 206, and a closed position, where the lid 210 can form a seal with the base 212. In certain embodiments, the seal can be a substantially fluid-tight seal formed by contact between respective faces of the lid 210 and the base 212 that can inhibit ingress of fluids and/or dust through the outer housing 202. The outer housing 202 can include attachment mechanisms 220 such as clasps, latches, and the like to facilitate sealing of the outer housing 202 when the lid 210 is closed.

The outer housing 202 can be formed from materials configured to protect the moisture analyzer from physical damage. As an example, the outer housing 202 can be formed from relatively strong and damage tolerant materials, such as metals, plastics, etc. In an exemplary embodiment, the outer housing 202 can be a Pelican™ case (Pelican Products, Inc., Torrance Calif.). However, in alternative embodiments (not shown), the outer housing can adopt other form factors without limit.

Figure 3:
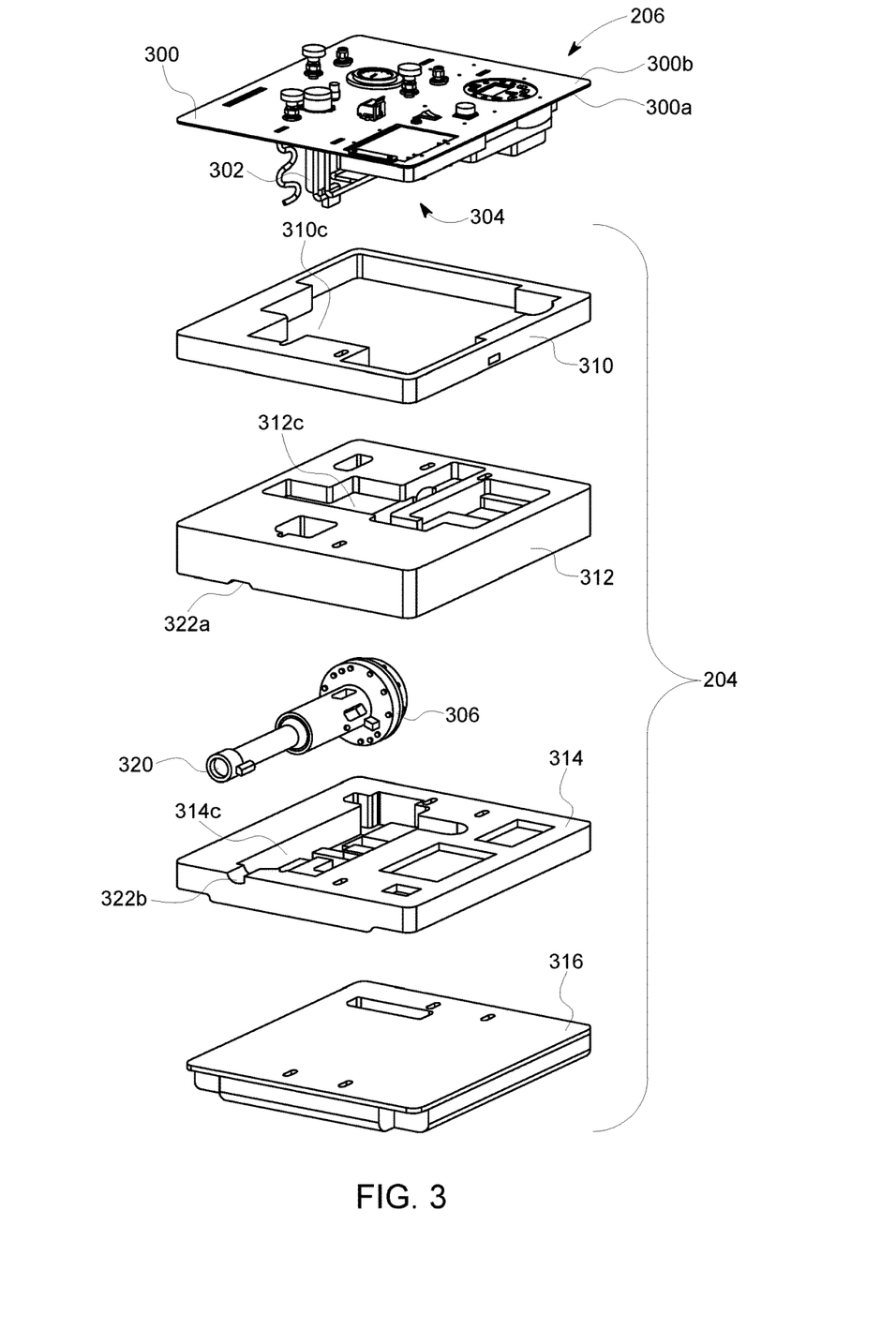
FIG. 3 is a perspective, disassembled view illustrating the inner housing and the moisture analyzer of FIG. 2.

FIG. 3 is a perspective, disassembled view illustrating the inner housing 204 and the moisture analyzer 206. The moisture analyzer 206 can include an instrument panel 300, a fluid conduit network 302, a sample conditioning system 304, and a moisture sensor 306. As discussed in greater detail below, the sample conditioning system 304 and a portion of the fluid conduit network 302 can be mounted to a first side 300a of the instrument panel 300 to improve the vibration and shock resistance of the moisture analyzer 206. User interfaces for control of the moisture analyzer 206 can also be mounted to a second side 300b of the instrument panel 300, opposite the first side 300a.

The inner housing 204 can be mounted to the first side 300a of the instrument panel 300 and encapsulate at least a portion of the moisture analyzer 206 (e.g., the fluid conduit network 302, the sample conditioning system 304, and the moisture sensor 306). Thus, when the moisture analyzer 206 and the inner housing 204 are placed within the outer housing 202, the moisture analyzer 206 can be substantially isolated from vibration and shock. The inner housing 204 can have any shape suitable for encapsulating at least a portion of the moisture analyzer 206, and for seating within the outer housing 202.

In an exemplary embodiment, the inner housing 204 can be formed from one or more layers of foam. The foam can be selected for one or more functional properties. In one aspect, the foam can be flame retardant (e.g., self-extinguishing). As an example, the foam can possess a predetermined flammability rating (e.g., UL 94 5VA). In another aspect, the foam can be anti-static and/or resistant to electrostatic discharge (ESD). In an additional aspect, the inner housing 204 can be configured to limit the free volume for combustible gas to leak, thereby minimizing flammability hazards and enhancing safety of the portable moisture analysis system. Suitable foam materials include, for example, cross-linked polyethylene. In certain embodiments, these features or other features of the foam can allow the portable moisture analyzer system 200 to meet the Class 1 Division 2/Zone 2 hazardous area certification as defined by the National Fire Protection Association (e.g., NFPA 70: National Electrical Code [NEC], 2017 edition) and/or codified in Title 29 of the Code of Federal Register (CFR) 1910.399. That is, embodiments of the portable moisture analysis system 200 can be certified for use in environments containing ignitable levels of flammable/explosive gas during faults.

In a further aspect, the foam can possess predetermined mechanical properties configured to absorb shock and vibration while being relatively light-weight. As discussed below, embodiments of the portable moisture analysis system 200 can be configured to weigh less than or equal to about 50 lbs., the one-man lift limit specified by the US Occupational Health and Safety Administration (OSHA).

As shown in FIG. 3, the inner housing 204 can include four layers 310, 312, 314, 316. A first layer 310 can be positioned adjacent to the instrument panel 300 and the first layer 310 can include a first inner housing cavity 310c. The first inner housing cavity 310c can extend through the thickness of the first layer 310, and the first inner housing cavity 310c can be dimensioned to receive the fluid conduit network 302 and the sample conditioning system 304 therethrough. A second layer 312 can be positioned adjacent to the first layer 310 and the second layer 312 can include one or more second inner housing cavities 312c. The second inner housing cavities 312c can be dimensioned to seat a portion of the fluid conduit network 302 and the sample conditioning system 304.

As shown in FIG. 3, the moisture sensor 306 can be interposed between the second layer 312 and a third layer 314. The third layer 314 can be positioned adjacent to the second layer 312, and the third layer 314 can include one or more third inner housing cavities 314c. The third housing inner cavities 314c can be dimensioned to seat a portion of the moisture sensor 306 (e.g., a lower portion). The second layer 312 can include additional inner housing cavities on a face opposite that containing the second inner housing cavities 312c (not shown) and these additional inner housing cavities of the third layer 314 can be configured to seat another portion of the moisture sensor 306 (e.g., an upper portion). A fourth layer 316 can be positioned adjacent to the third layer 314 and opposite the second layer 312.

In certain embodiments, the moisture sensor 306 can be in the form of a tunable diode laser absorption spectrometer (TDLAS). Embodiments of a TDLAS moisture sensor are discussed in detail in U.S. Provisional Patent Application No. 62/310,333, filed on Mar. 18, 2016, and entitled "Fluid Analyzer Absorption Cell," the entirety of which is hereby incorporated by reference. In brief, a TDLAS can receive a natural gas sample within an absorption cell and pass laser light having different wavelengths through the natural gas sample. The TDLAS can include a mirror 306m at one end that is configured to reflect the light so as to increase the path length of the light and improve sensitivity of the TDLAS. The amount of light absorbed at different wavelengths can be measured to generate an absorption spectrum and peaks within the measured absorption spectrum corresponding to moisture and natural gas can be identified. According to Beer's Law, the amount of light absorbed by the natural gas sample can be proportional to the amount of water vapor present in the path of the light, providing a direct measurement of moisture content that can be represented in data output by the TDLAS in the form of one or more signals.

Embodiments of the TDLAS can provide a number of advantages over other moisture sensors. In one aspect, because the TDLAS employs light to measure moisture content of the natural gas sample, the TDLAS can measure changes in the moisture concentration of the natural gas sample very rapidly. In another aspect, the response time of the TDLAS can be limited only by the time required for the natural gas sample to travel through the fluid conduit network to the TDLAS. As an example, the response time of the TDLAS can be less than about 10 sec. In a further aspect, the calibration of the TDLAS can remain stable for extended time periods (e.g., years), avoiding the need for frequent calibration that can be present in aluminum oxide moisture probes. In an additional aspect, the TDLAS does not require differential measurement (e.g., with a scrubber to remove moisture content) as found in quartz crystal microbalance (QCM)-based analyzers. In another aspect, when employed to measure conditioned sample flows, as discussed in detail below, the TDLAS can provide parts per million by volume (PPMv)-level accuracy and repeatability. This level of accuracy and reproducibility can be comparable to state-of-the-art fixed site and laboratory analyzers.

Figure 4:
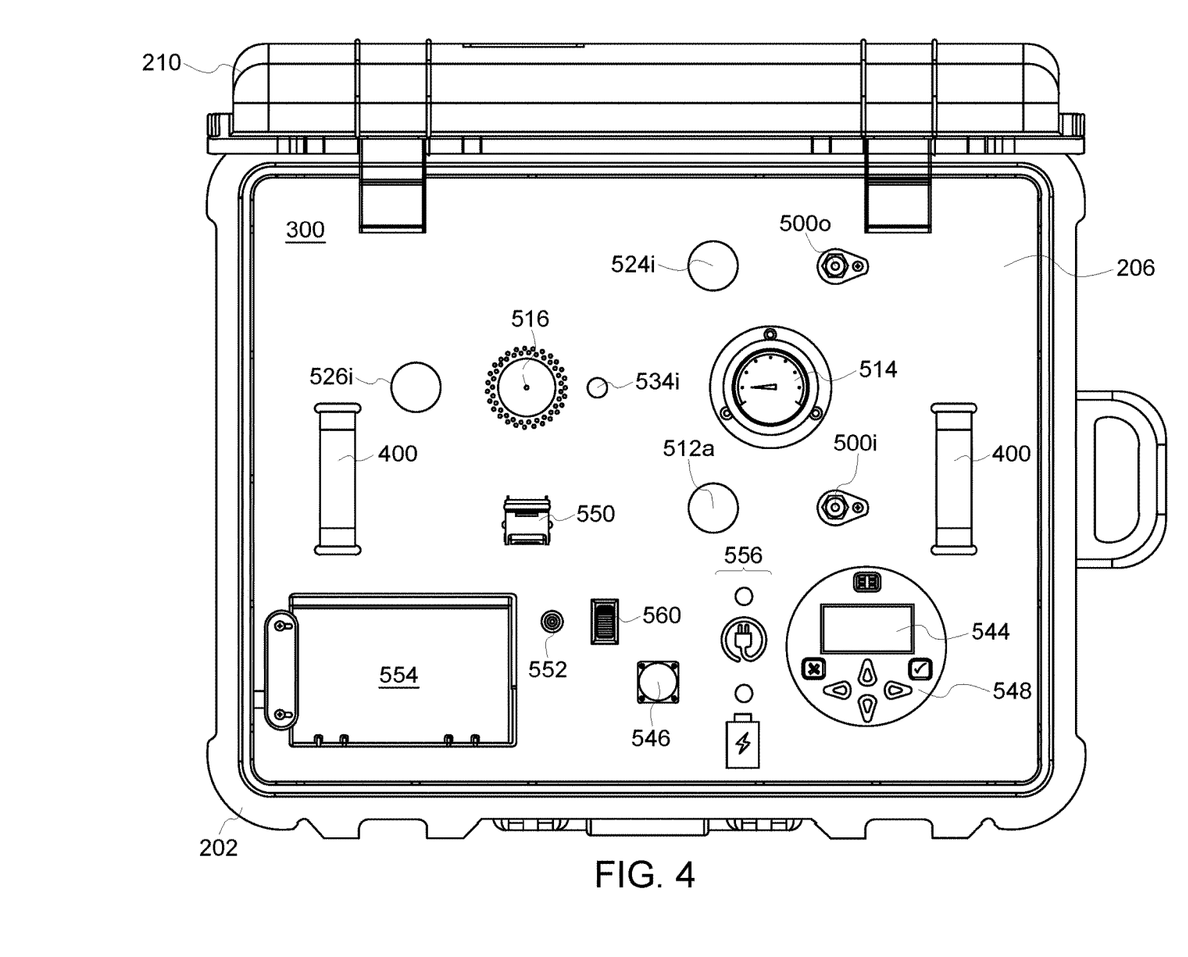
FIG. 4 is a schematic diagram illustrating one exemplary embodiment of an instrument panel of the moisture analyzer of FIG. 2.
Figure 5:
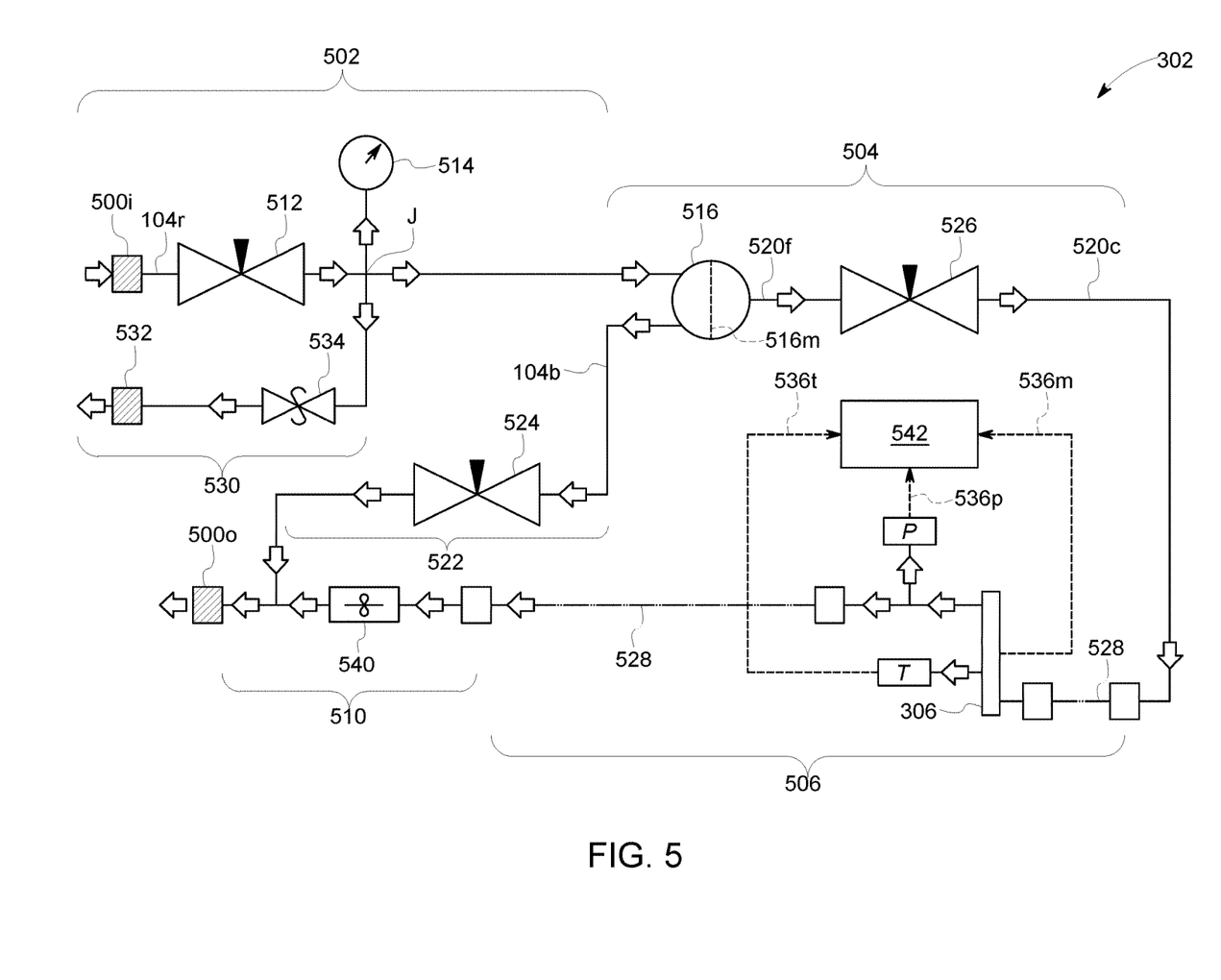
FIG. 5 is a schematic diagram illustrating one exemplary embodiment of a fluid conduit network of the moisture analyzer of FIG. 2.

FIG. 4 is a schematic diagram illustrating an exemplary embodiment of the instrument panel 300 and is discussed in conjunction with an embodiment of the fluid conduit network 302 illustrated in FIG. 5. As shown, the fluid conduit network 302 can include an inlet 500i and an outlet 500o accessible from the second side 300b of the instrument panel 300. The inlet 500i and the outlet 500o can each be configured to fluidly couple to a gas source such as a natural gas pipeline via a fluid line (not shown) at the instrument panel 300. The inlet 500i and the outlet 500o can further employ a quick connect/quick release mechanism to facilitate coupling to the gas source.

The fluid conduit network 302 can include a plurality of conduits extending from the inlet 500i to the outlet 500o and the conduits can form an inlet portion 502, a conditioning portion 504, a sensor portion 506, and an outlet portion 510. At least a portion of the fluid conduit network 302 can be mounted to the first side 300a of the instrument panel 300 and, as discussed in detail below, a variety of flow control valves can be positioned along the fluid conduit network 302 for regulating flow of natural gas therethrough. The valves can be further controlled by interfaces accessible from the second face of the instrument panel 300.

The inlet portion 502 of the fluid conduit network 302 can extend between the inlet 500i and the conditioning portion 504 and it can be mounted on the first side 300a of the instrument panel 300. As shown, the inlet portion 502 includes an isolation valve 512 configured to allow or inhibit the raw sample flow 104r from flowing through the inlet portion 502 under control of an isolation control interface 512i accessible from the second side 300b of the instrument panel 300. In certain embodiments, the isolation control interface 512i can be a rotatable knob coupled to the isolation valve 512.

The inlet portion 502 can also include a junction (union) J that is in fluid communication with an inlet pressure gage 514. The inlet pressure gage 514 can be configured to measure a pressure of the raw sample flow 104r prior to receipt by the conditioning portion 504. The inlet pressure gage 514 can also be mounted to the instrument panel 300 and the inlet pressure gage 514 can be readable from the second side 300b of the instrument panel 300. So configured, a user can monitor an inlet pressure of the raw sample flow 104r entering the moisture analyzer 206 from the gas source using the inlet pressure gage 514 and the user can turn on or off the raw sample flow 104r using the isolation control interface 512i.

The conditioning portion 504 can extend between the inlet portion 502 and the sensor portion 506 and it can be mounted on the first side 300a of the instrument panel 300. One or more conditioning devices of the sample conditioning system 304 can be positioned along the conditioning portion 504 for conditioning the raw sample flow 104r. In an embodiment, the one or more conditioning devices can include a separator 516 configured to filter liquids from the raw sample flow 104r and provide a filtered sample flow 520f having a liquid content less than a threshold liquid volume. In certain embodiments, the separator 516 can include a membrane filter 516m to filter out particulate contamination in the gas sample, and the membrane filter 516m can be accessible through the second side 300b of the instrument panel 300 for servicing, such as removal, replacement, and repair.

The fluid conduit network 302 can optionally include a bypass portion 522 extending between the separator 516 and the outlet 500o. The bypass portion 522 can be configured to receive a bypass flow 104b at a bypass flow rate including liquids filtered from the raw sample flow 104. The bypass portion 522 can also include a bypass valve 524 configured to regulate the bypass flow rate under control of a bypass control interface 524i accessible from the second side 300b of the instrument panel 300.

The separator 516 can also be configured to substantially inhibit a flow of the raw sample flow 104r causing a pressure drop exceeding a threshold pressure decrease from entering the conditioning portion 504. As an example, the membrane filter 516m can be configured to block a passage therethrough when the raw sample flow 104r causes a pressure decrease exceeding the threshold pressure drop.

The one or more conditioning devices can also include a sample valve 526 interposed between the separator 516 and the moisture sensor 306. The sample valve 526 can be configured to regulate a flow rate of the filtered sample flow under control of a sample control interface 526i accessible from the second side 300b of the instrument panel 300. In this manner, a conditioned sample flow 520c having a flow rate within a predetermined flow rate range can be provided to the moisture sensor 306. Furthermore, the bypass valve 524 and the sample valve 526 can provide independent control of the flow rates of the bypass flow 104b and the conditioned sample flow 520c such that the pressure of the conditioned sample flow 520c can be regulated to achieve a predetermined pressure range or target (e.g., about 1 atm.).

The fluid conduit network 302 can also include a relief portion 530 extending between the junction J and a relief outlet 532. The relief portion 530 can include a relief vent 534 configured to permit flow of the raw sample flow 104r from the inlet portion 502 to the relief outlet 532 under control of a relief control interface 534i that is accessible from the second side 300b of the instrument panel 300. In certain embodiments, the relief control interface 534i can be a button or knob. In certain embodiments, the relief valve 534 can be a check valve configured to automatically open when the inlet pressure exceeds a predetermined value (e.g., about 50 psig). So configured, accidental over-pressurization of the inlet portion 502 can be avoided.

The sensor portion 506 can extend between the conditioning portion 504 and the outlet portion 510 and the moisture sensor 306 can be positioned along the sensor portion 506. As discussed above, the moisture sensor 306 can be a TDLAS and it can be configured to detect water vapor content within the conditioned sample flow and output a moisture signal 536m including data representing the measured water vapor content. In contrast to the other portions of the fluid conduit network 302 (e.g., 502, 504, 510), part or all of the sensor portion 506 can be distanced from the instrument panel 300. This configuration can reflect that the moisture sensor 306 is not mounted to the instrument panel 300 but instead embedded within the inner housing 204 for vibration isolation. To further facilitate vibration isolation of the moisture sensor 306, at least a portion of the conduits of the sensor portion 506 can be formed from a material that is more compliant than a material forming the conduits of the other portions of the fluid conduit network 502, 504, 510. As an example, the conduits forming the inlet portion 502, the conditioning portion 504, and the outlet portion 510 can be formed from a steel or steel alloy (e.g., a stainless steel alloy such as 316L SS), while the relatively flexible conduits 528 of the sensor portion 506 can be formed from a plastic (PTFE)-lined stainless steel braided hose assembly. Other materials having comparatively rigid and flexible mechanical properties are also contemplated.

The sensor portion 506 can also include one or more additional sensors. In one aspect, the sensor portion can include a temperature sensor T configured to output a temperature signal including data representing a measured temperature of a conditioned sample flow 520c received by the moisture sensor 306. The temperature sensor T can be in thermal communication with the moisture sensor 306 for measuring the temperature of the conditioned sample flow 520c. In another aspect, the sensor portion 506 can include a pressure sensor P configured to output a pressure signal 536p including data representing a measured pressure of the conditioned sample flow 520c received by the moisture sensor 306. The pressure sensor P can be in hydraulic communication with the moisture sensor 306 for measuring the pressure of the conditioned sample flow 520c.

The outlet portion 510 can extend between the sensor portion 506 and the outlet 500o and the outlet portion 510 can be mounted on the second side 300b of the instrument panel 300. In certain embodiments, a flow meter 540 can be positioned within the outlet portion 510, prior to the outlet 500o, for measurement of the flow rate of the conditioned sample flow 520c. As an example, the flow meter 540 can be a mass flow meter. Beneficially, in contrast to rotameters, a mass flow meter can be insensitive to orientation, allowing the portable moisture analyzer system 200 to be mounted in any orientation.

Embodiments of the valves are discussed above with reference to manually actuatable valves. However, in alternative embodiments, valves having other actuation and control mechanisms can be employed without limit, such as electronically controlled valves.

In further embodiments, moisture analyzer 206 can further include electronics for acquiring, analyzing, storing, and/or communicating the sensor measurements. In one aspect, the moisture analyzer 206 can include a controller 542 mounted to the second side 300b of the instrument panel 300. The controller 542 can be in communication with the moisture sensor 306, the pressure sensor P, and the temperature sensor T. The controller 542 can be configured to receive the moisture signal 536m. In certain embodiments, the controller 542 can include a processor, memory, and/or other components necessary to execute instructions capable of determining the moisture content from the moisture signal 536m.

Generally, analysis of the moisture signal 536m can assume conditions of standard temperature and pressure (e.g., a temperature of about 25° C. and a pressure of about 1 atm.). Under circumstances where the temperature and pressure of the conditioned sample flow 520c deviate from standard temperature and pressure, such deviations can introduce error into the moisture content measurement. Accordingly, the controller 542 can also be configured to receive the pressure signal 536p and the temperature signal 536t, and the controller 542 can also generate an adjusted moisture content measurement based upon the measured temperature and pressure.

The controller 542 can also be in communication with one or more human-machine interfaces (HMIs), such as a display 544 (e.g., a digital display such as an LCD), an input/output 546 (e.g., analog or digital), a keypad 548, and a network connection 550 (e.g., serial RS-232/RS-485, Ethernet). Measurements of pressure, temperature, and moisture content can be transmitted to any of these interfaces for further display or storage. In some instances, a user can act upon the measurements provided to alter or improve the system.

Further embodiments of the instrument panel 300 can be configured to receive electrical power from a power source for operating electrical components of the moisture analyzer. In certain embodiments, the instrument panel 300 can include a power input connector 552 for receiving electrical power from power sources such as AC mains, DC (e.g., automotive), solar, and the like. In other embodiments, the power source can be a battery 554. As an example, the battery 554 can be a rechargeable battery (e.g., a Li-ion battery) that can allow operation of the portable moisture analyzer system without recharging from a power source for a predetermined amount of time (e.g., about 10 hours) before requiring charging. Embodiments of the battery 554 can be configured for charging from power sources such as AC mains, DC (e.g., automotive), solar, and the like. Embodiments of the battery 554 can also be configured for removal from the instrument panel 300 to facilitate compliance with air cargo transport regulations and in-field replacement. As shown in FIG. 4, the instrument panel 300 can also include indicators 556 (e.g., lights) for charge progress, charge completion, and remaining battery life (not shown). A power interface 560 (e.g., a switch) can control the powered state of the moisture analyzer 206 (e.g., off or on).

The instrument panel 300 can also be configured to allow the moisture analyzer 206 to be serviced, off-line or in-service. In one aspect, the instrument panel 300 can include handles 400 to facilitate removal of the moisture analyzer 206 from the outer housing 202 and/or the inner housing 204. In another aspect, discussed above, the battery 554 and/or the separator 516 can be removed from the moisture analyzer 206. As an example, the separator 516 can include a removable cap mounted to the second side 300b of the instrument panel 300 that can allow access to the membrane filter 516m. Removal of the cap can allow the membrane filter 516m to be replaced.

In further embodiments, the moisture sensor 306 can be configured to permit cleaning and/or replacement of optical components such as the end mirror 306m of a TDLAS cell, as discussed in U.S. Provisional Application No. 62/310,333. Generally, trace liquids and/or solid contaminants contained within the raw sample flow 104r can pass through the separator 516 and they can deposit on the mirror 306m of the absorption cell of the TDLAS over time, partially or totally blocking the mirror 306m. The mirror 306m can be attached to a reversibly attachable portion 320 of the moisture analyzer 206 and the inner housing 204 can include a channel 322 extending through a sidewall that is dimensioned for receipt of the reversibly attachable portion 320. As shown in FIG. 3, the channel 322 is split into a first channel portion 322a formed within the second layer 312 and a second channel portion 322b formed within the third layer 314. The TDLAS sample absorption cell can be positioned within the inner housing 204 such that the reversibly attachable portion 320 is accessible through the channel 322. In this manner, the reversibly attachable portion 320 can be detached from the TDLAS absorption cell, removed from the inner housing 204 via the channel 322, cleaned, and reattached to the TDLAS.

Figure 6A:
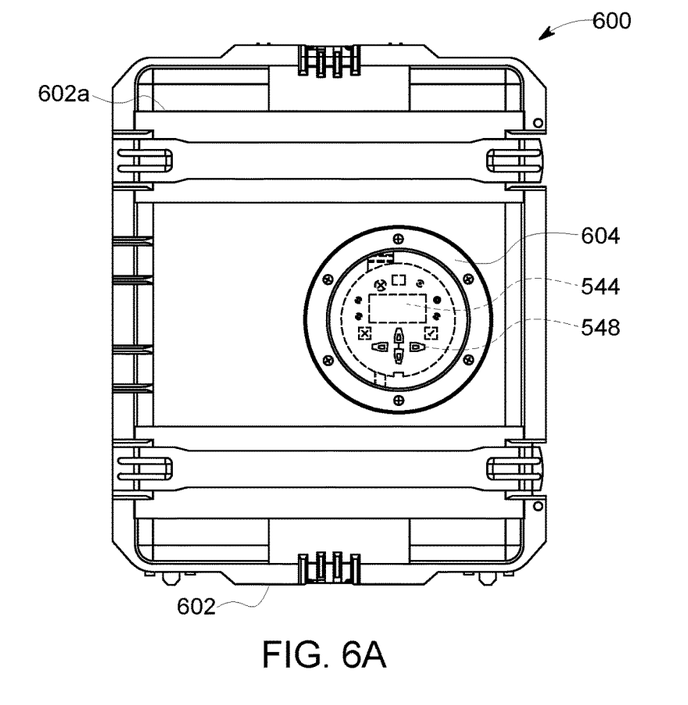
FIG. 6A is a top view illustrating another exemplary embodiment of the portable moisture analyzer system of FIG. 1.
Figure 6B:
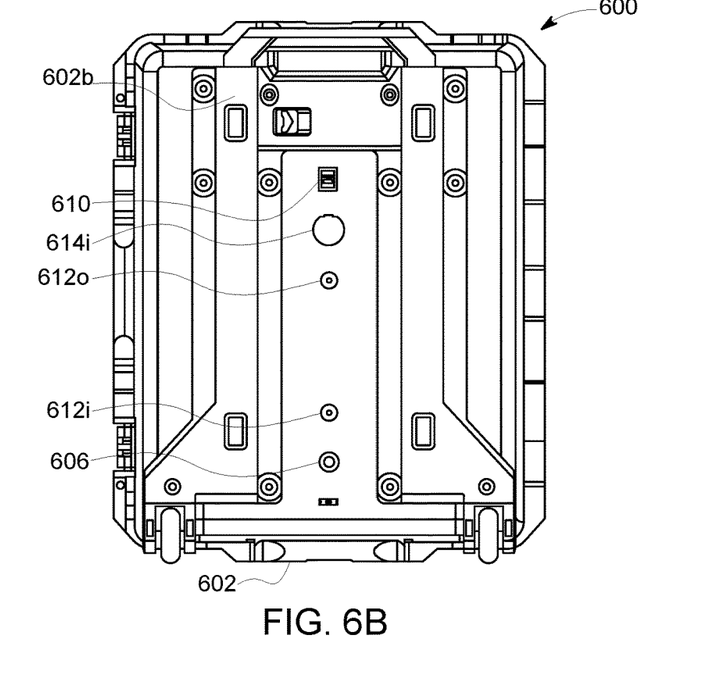
FIG. 6B is a bottom view illustrating another exemplary embodiment of the portable moisture analyzer system of FIG. 1.

FIGS. 6A-6B are schematic diagrams illustrating top and bottom views of another embodiment of a portable moisture analyzer system 600 including an outer housing 602. The portable moisture analyzer system 600 can be modified with respect to the portable moisture analyzer system 200 in order to allow visualization and/or access to certain components mounted to the instrument panel 300 without opening the outer housing 602. Because the outer housing 602 can provide a seal that prevents ingress of particles and/or liquids, similar to the outer housing 202, the portable moisture analyzer system 600 can be employed on-site for moisture content measurements for extended time periods (e.g., hours, days, months, weeks, etc.) without a user present.

As shown in FIG. 6A, a top surface 602a of the portable moisture analyzer system 600 can include a display port 604 (e.g., a substantially transparent window) allowing visualization of the display 544 and the keypad 548. In certain embodiments, the display port 604 can be removed for access to the display 544 and keypad 548. In other embodiments, the display 544 and/or the keypad 548 can be configured for touchless actuation (e.g., magnetic), allowing a user to interact with the display 544 and/or the keypad 548 without removing the display port 604 or opening the outer housing 602.

As shown in FIG. 6B, a bottom surface 602b of the portable moisture analyzer system 600 can include a power input connector 606, a power interface 610, an inlet 612i, an outlet 612o, and an isolation control interface 614i. Each of these components can operate similarly to their counterparts in the portable moisture analyzer system 600 (e.g., power input connector 552, power interface 560, inlet 500i, outlet 500o, and isolation control interface 512i).

Figure 7:
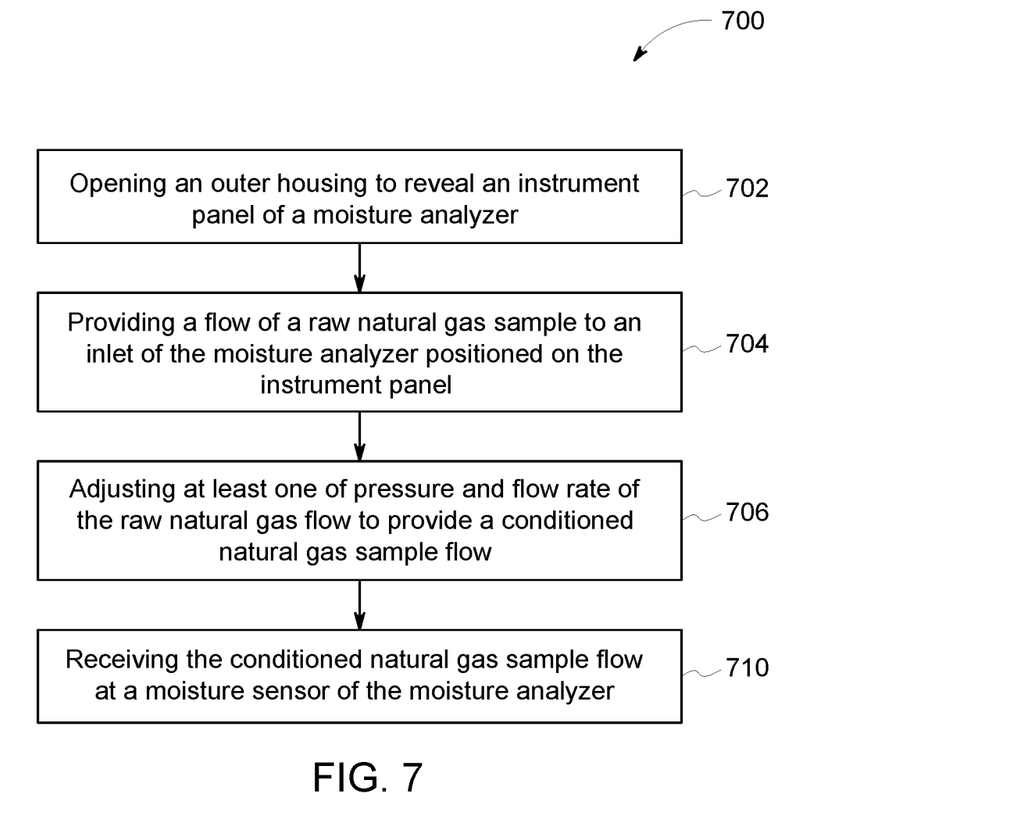
FIG. 7 is a flow diagram illustrating one exemplary embodiment of a method for moisture analysis of a natural gas sample.

FIG. 7 is a flow diagram illustrating an exemplary embodiment of a method 700 for moisture analysis of natural gas samples. The method 700 described below can be employed in conjunction with either of the portable moisture analyzer systems 200, 600.

In operation 702, a reversibly sealable outer housing of a moisture analyzer system is opened to reveal an instrument panel. In certain embodiments, the outer housing can include a lid and a base and the outer housing can be opened by moving the lid.

In operation 704, a raw natural gas sample flow at a raw gas pressure and a raw gas flow rate can be provided from a natural gas source to an inlet of the moisture analyzer positioned on the instrument panel.

In operation 706, at least one of the raw gas pressure and the raw gas flow rate of the raw sample flow can be adjusted to provide a conditioned sample flow. As an example, the raw sample flow can be adjusted by a sample conditioning system of the moisture analyzer disposed within an outer housing cavity in the outer housing. At least a portion of a sample conditioning system can be mounted to a first side of the instrument panel of the moisture analyzer, and one or more user interface objects configured to control the sample conditioning system can be mounted to a second side of the instrument panel.

In operation 710, a moisture sensor can receive the conditioned natural gas sample from the sample conditioning system. The moisture sensor can be mounted within, and spaced apart from, an inner housing mounted to the first side of the instrument panel. The outer housing and the inner housing can be configured to attenuate vibration and/or shock transmitted therethrough to the moisture sensor.

Exemplary technical effects of the methods, systems, and devices described herein can include, by way of non-limiting example, portable moisture analysis of natural gas within transport networks. In one aspect, embodiments of the disclosed portable moisture analyzer system can provide conditioning of natural gas samples prior to moisture content measurement. This conditioning can provide accurate and repeatable measurements of moisture content. In another aspect, embodiments of the disclosed portable moisture analyzer system can be self-contained and rugged enough to be transported from one test point to another on a natural gas transport/storage network (e.g., a pipeline). As an example, the portable moisture analyzer system can be able to withstand transport vibration and shock while preserving sample conditioning functionality, optical alignment, and safety. In a further aspect, user inputs and controls can be mounted to an instrument panel for ease of access while vibration sensitive optical components and electronics are immersed in vibration damping and flame-retardant material (e.g., foam) to improve vibration and impact resistance.

The subject matter described herein can be implemented in analog electronic circuitry, digital electronic circuitry, and/or in computer software, firmware, or hardware, including the structural means disclosed in this specification and structural equivalents thereof, or in combinations of them. The subject matter described herein can be implemented as one or more computer program products, such as one or more computer programs tangibly embodied in an information carrier (e.g., in a machine-readable storage device), or embodied in a propagated signal, for execution by, or to control the operation of, data processing apparatus (e.g., a programmable processor, a computer, or multiple computers). A computer program (also known as a program, software, software application, or code) can be written in any form of programming language, including compiled or interpreted languages, and it can be deployed in any form, including as a stand-alone program or as a module, component, sub-routine, or other unit suitable for use in a computing environment. A computer program does not necessarily correspond to a file. A program can be stored in a portion of a file that holds other programs or data, in a single file dedicated to the program in question, or in multiple coordinated files (e.g., files that store one or more modules, sub-programs, or portions of code). A computer program can be deployed to be executed on one computer or on multiple computers at one site or distributed across multiple sites and interconnected by a communication network.

The processes and logic flows described in this specification, including the method steps of the subject matter described herein, can be performed by one or more programmable processors executing one or more computer programs to perform functions of the subject matter described herein by operating on input data and generating output. The processes and logic flows can also be performed by, and apparatus of the subject matter described herein can be implemented as, special purpose logic circuitry, e.g., an FPGA (field programmable gate array) or an ASIC (application-specific integrated circuit).

Processors suitable for the execution of a computer program include, by way of example, both general and special purpose microprocessors, and any one or more processor of any kind of digital computer. Generally, a processor will receive instructions and data from a read-only memory or a random access memory or both. The essential elements of a computer are a processor for executing instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. Information carriers suitable for embodying computer program instructions and data include all forms of non-volatile memory, including by way of example semiconductor memory devices, (e.g., EPROM, EEPROM, and flash memory devices); magnetic disks, (e.g., internal hard disks or removable disks); magneto-optical disks; and optical disks (e.g., CD and DVD disks). The processor and the memory can be supplemented by, or incorporated in, special purpose logic circuitry.

To provide for interaction with a user, the subject matter described herein can be implemented on a computer having a display device, e.g., a CRT (cathode ray tube) or LCD (liquid crystal display) monitor, for displaying information to the user and a keyboard and a pointing device, (e.g., a mouse or a trackball), by which the user can provide input to the computer. Other kinds of devices can be used to provide for interaction with a user as well. For example, feedback provided to the user can be any form of sensory feedback, (e.g., visual feedback, auditory feedback, or tactile feedback), and input from the user can be received in any form, including acoustic, speech, or tactile input.

The techniques described herein can be implemented using one or more modules. As used herein, the term "module" refers to computing software, firmware, hardware, and/or various combinations thereof. At a minimum, however, modules are not to be interpreted as software that is not implemented on hardware, firmware, or recorded on a non-transitory processor readable recordable storage medium (i.e., modules are not software per se). Indeed "module" is to be interpreted to always include at least some physical, non-transitory hardware such as a part of a processor or computer. Two different modules can share the same physical hardware (e.g., two different modules can use the same processor and network interface). The modules described herein can be combined, integrated, separated, and/or duplicated to support various applications. Also, a function described herein as being performed at a particular module can be performed at one or more other modules and/or by one or more other devices instead of or in addition to the function performed at the particular module. Further, the modules can be implemented across multiple devices and/or other components local or remote to one another. Additionally, the modules can be moved from one device and added to another device, and/or can be included in both devices.

The subject matter described herein can be implemented in a computing system that includes a back-end component (e.g., a data server), a middleware component (e.g., an application server), or a front-end component (e.g., a client computer having a graphical user interface or a web browser through which a user can interact with an implementation of the subject matter described herein), or any combination of such back-end, middleware, and front-end components. The components of the system can be interconnected by any form or medium of digital data communication, e.g., a communication network. Examples of communication networks include a local area network ("LAN") and a wide area network ("WAN"), e.g., the Internet.

Approximating language, as used herein throughout the specification and claims, may be applied to modify any quantitative representation that could permissibly vary without resulting in a change in the basic function to which it is related. Accordingly, a value modified by a term or terms, such as "about," "approximately," and "substantially," are not to be limited to the precise value specified. In at least some instances, the approximating language may correspond to the precision of an instrument for measuring the value. Here and throughout the specification and claims, range limitations may be combined and/or interchanged, such ranges are identified and include all the sub-ranges contained therein unless context or language indicates otherwise.

Certain exemplary embodiments will have been described to provide an overall understanding of the principles of the structure, function, manufacture, and use of the systems, devices, and methods disclosed herein. One or more examples of these embodiments have been illustrated in the accompanying drawings. Those skilled in the art will understand that the systems, devices, and methods specifically described herein and illustrated in the drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention. Further, in the present disclosure, like-named components of the embodiments generally have similar features, and thus within a particular embodiment each feature of each like-named component is not necessarily fully elaborated upon.

One skilled in the art will appreciate further features and advantages of the invention based on the above-described embodiments. Accordingly, the present application is not to be limited by what has been particularly shown and described, except as indicated by the appended claims. All publications and references cited herein are expressly incorporated by reference in their entirety.

What is claimed is:

1. A portable moisture analyzer system, comprising:
   a moisture analyzer including,
      a moisture sensor configured to detect water vapor content within a gas sample and output a moisture signal including data representing the detected water vapor content,
      a fluid conduit network in fluid communication with the moisture sensor and extending between an inlet and an outlet, wherein the fluid conduit network is configured to receive, at the inlet, a flow of a raw gas sample from a sample gas source at a raw flow rate;
      one or more conditioning devices positioned within the fluid conduit network between the inlet and the moisture sensor, wherein the conditioning devices include one or more valves configured to adjust at least one of pressure and flow rate of a raw gas sample flow received by the fluid conduit network and a separator configured to filter particulate and liquid contaminants from the raw gas sample flow to provide a conditioned gas sample flow to the moisture sensor, and
      an instrument panel including opposed first and second sides, wherein each of the conditioning devices and a portion of the fluid conduit network are mounted on the first side of the instrument panel,
      an inner housing defining one or more inner housing cavities dimensioned to receive a portion of the moisture analyzer including the moisture sensor, wherein the inner housing is coupled to the first side of the instrument panel; and
      an outer housing defining an outer housing cavity dimensioned to receive the inner housing and the moisture analyzer;
      wherein the outer housing and the inner housing are configured to attenuate vibration transmitted therethrough to the moisture sensor.

2. The portable moisture analyzer system of claim 1, wherein the outer housing includes a base and a lid configured to reversibly seal to the base, and wherein the outer housing is substantially fluid-tight when the lid is sealed to the base.

3. The portable moisture analyzer of claim 1, wherein the moisture sensor comprises a laser absorption spectrometer.

4. The portable moisture analyzer of claim 3, wherein the spectrometer comprises a reversibly attachable portion including a mirror, wherein the inner housing further comprises a channel extending through a sidewall that is dimensioned for receipt of the reversibly attachable portion, and wherein the spectrometer is positioned within the inner housing such that the reversibly attachable portion is accessible through the channel.

5. The portable moisture analyzer of claim 1,
   wherein the fluid conduit network comprises a plurality of conduits forming an inlet portion, a conditioning portion, a sensor portion, and an outlet portion;
   wherein the inlet portion extends between the inlet and the conditioning portion and is mounted on the first side of the instrument panel;
   wherein the conditioning portion extends between the inlet portion and the sensor portion and is mounted on the first side of the instrument panel, and wherein the conditioning devices are positioned within the conditioning portion;
   wherein the sensor portion extends between the conditioning portion and the outlet portion, and wherein the moisture sensor is positioned along the sensor portion; and
   wherein the outlet portion extends between the sensor portion and the outlet and is mounted on the first side of the instrument panel.

6. The portable moisture analyzer of claim 5, wherein the inlet portion comprises an isolation valve configured to regulate the raw flow rate within the moisture analyzer under control of an isolation control interface accessible from the second side of the instrument panel.

7. The portable moisture analyzer of claim 5, wherein the inlet portion further comprises an inlet pressure gage configured to measure a pressure of the raw gas sample flow prior to receipt by the conditioning portion, and wherein the inlet pressure gage is mounted to the instrument panel and readable from the second side of the instrument panel.

8. The portable moisture analyzer system of claim 5, wherein the separator is configured to filter liquids from the raw gas sample flow and provide a filtered gas sample flow having a liquid content less than a threshold liquid volume.

9. The portable moisture analyzer system of claim 8, wherein the fluid conduit network further comprises a bypass portion extending between the first conditioning device and the outlet that includes a bypass valve, wherein the bypass portion is configured to receive a bypass flow including liquids filtered from the raw gas sample at a bypass flow rate, and the bypass valve is configured to regulate the bypass flow rate under control of a bypass control interface accessible from the second side of the instrument panel.

10. The portable moisture analyzer system of claim 8, wherein the separator is accessible through the second side of the instrument panel for removal from the system.

11. The portable moisture analyzer system of claim 8, wherein the separator is further configured to substantially inhibit a flow of a raw gas sample causing a pressure drop exceeding a threshold pressure decrease from entering the conditioning portion.

12. The portable moisture analyzer of claim 8,
wherein the sample valve is interposed between the separator and the moisture sensor, and
wherein the sample valve is configured to regulate a flow rate of the filtered gas sample flow under control of a sample control interface accessible from the second side of the instrument panel to provide a conditioned gas sample flow having a flow rate within a predetermined flow rate range.

13. The portable moisture analyzer system of claim 5, wherein the fluid conduit network further comprises a relief portion extending between the inlet portion and a relief outlet and a relief vent positioned along the relief portion, and wherein the relief vent is configured to permit the flow of raw gas from the inlet portion to the relief outlet under control of a relief control interface accessible from the second side of the instrument panel.

14. The portable moisture analyzer of claim 5, wherein the plurality of conduits comprises a first set of conduits forming the inlet portion, the conditioning portion, and outlet portion and a second set of conduits forming the sensor portion, and wherein at least a portion of the second set of conduits is less rigid than the second set of conduits.

15. The portable moisture analyzer of claim 1, further comprising:
a temperature sensor configured to output a temperature signal including data representing a measured temperature of a conditioned gas sample flow received by the moisture sensor;
a pressure sensor configured to output a pressure signal including data representing a measured pressure of a conditioned gas sample flow received by the moisture sensor; and
a controller configured to,
receive the moisture signal, the temperature signal and the pressure signal, and
determine an adjusted moisture content for the conditioned gas sample flow based upon the received moisture signal, temperature signal, and pressure signal.

16. The portable moisture analyzer of claim 1, wherein the weight of the portable moisture analyzer system is less than or equal to 50 lbs.

17. A method of moisture analysis, comprising:
opening a reversibly sealable outer housing of a moisture analyzer system to reveal an instrument panel;
providing, from a gas source to an inlet of the moisture analyzer positioned on the instrument panel, a raw gas sample flow at a raw gas pressure and a raw gas flow rate;
adjusting, by one or more valves of a sample conditioning system of a moisture analyzer disposed within an outer housing cavity in the outer housing, at least one of the raw gas pressure and the raw gas flow rate to provide a conditioned gas sample flow, wherein at least a portion of the sample conditioning system is mounted to a first side of an instrument panel of the moisture analyzer, and one or more user interface objects configured to control the sample conditioning system are mounted to a second side of the instrument panel;
receiving, by a moisture sensor of the moisture analyzer, the conditioned gas sample from the sample conditioning system, wherein the moisture sensor is mounted within and spaced apart from an inner housing mounted to the first side of the instrument panel, and wherein the outer housing and the inner housing are configured to attenuate vibration transmitted therethrough to the moisture sensor.

18. The method of claim 17, further comprising:
receiving, by a controller in communication with the moisture sensor, a moisture signal, a pressure signal, and a temperature signal, each signal respectively including data representing a moisture content, a pressure, and a temperature of the conditioned gas sample flow received by the moisture sensor; and
determining, by the controller, an adjusted moisture content based upon the received moisture signal, temperature signal, and pressure signal.

19. The method of claim 17, wherein the gas source is a natural gas pipeline.

20. The method of claim 19, further comprising, prior to providing the raw gas sample flow to the inlet of the moisture analyzer, transporting the moisture analyzer system to the site of the gas pipeline, wherein the portable moisture analyzer weighs less than or equal to fifty lbs.

21. The method of claim 17,
wherein the moisture sensor includes a spectrometer including a reversibly attachable portion including a mirror,
wherein the inner housing further includes a channel extending through a sidewall that is dimensioned for receipt of the reversibly attachable portion, and
wherein the spectrometer is positioned within the inner housing such that the reversibly attachable portion is accessible through the channel when the inner housing and the moisture analyzer are removed from the outer housing while coupled together.

* * * * *